United States Patent
Müller et al.

(10) Patent No.: US 7,591,948 B2
(45) Date of Patent: Sep. 22, 2009

(54) PROCESS FOR PRODUCTION OF A REGIOSELECTIVE MEMBRANE

(75) Inventors: Michael Müller, Stuttgart (DE); Christian Oehr, Herrenberg (DE); Heinrich Malthaner, Stuttgart (DE); Hermann Goehl, Bisingen-Zimmern (DE); Reinhold Deppisch, Hechingen (DE); Markus Storr, Leinfelden-Echterdingen (DE)

(73) Assignees: Gambro Lundia AB, Lund (SE); Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 437 days.

(21) Appl. No.: 10/511,471

(22) PCT Filed: Apr. 23, 2003

(86) PCT No.: PCT/SE03/00655

§ 371 (c)(1),
(2), (4) Date: May 3, 2005

(87) PCT Pub. No.: WO03/090910

PCT Pub. Date: Nov. 6, 2003

(65) Prior Publication Data

US 2005/0214162 A1    Sep. 29, 2005

(30) Foreign Application Priority Data

Apr. 23, 2002    (SE)    .................................... 0201207

(51) Int. Cl.
 *B01D 61/00*    (2006.01)
 *B01D 63/00*    (2006.01)
 *B01D 39/14*    (2006.01)
 *H05H 1/24*    (2006.01)

(52) U.S. Cl. ............. 210/645; 210/500.23; 210/500.37; 210/321.8; 210/321.75; 427/569; 264/48; 435/135

(58) Field of Classification Search ................. 210/507, 210/645, 490, 483, 500.27, 500.37, 500.42, 210/500.23, 500.41, 321.8, 321.75; 424/422; 264/41, 22, 98.8, 98.9, 48; 427/488, 483, 427/569; 435/135, 180; 521/53
See application file for complete search history.

(56) References Cited

U.S. PATENT DOCUMENTS

| | | | |
|---|---|---|---|
| 4,290,987 A * | 9/1981 | Soehngen et al. ............. 264/41 |
| 5,202,025 A | 4/1993 | Onishi et al. | |
| 5,547,576 A * | 8/1996 | Onishi et al. ........... 210/500.37 |
| 5,591,140 A | 1/1997 | Narayanan et al. | |
| 5,597,456 A | 1/1997 | Maruyama et al. | |
| 5,766,908 A | 6/1998 | Klein et al. | |
| 5,840,190 A * | 11/1998 | Scholander et al. .... 210/500.24 |

(Continued)

FOREIGN PATENT DOCUMENTS

EP    0683197 B1    7/1999

(Continued)

*Primary Examiner*—Ana M Fortuna
(74) *Attorney, Agent, or Firm*—Greenlee Winner and Sullivan, P.C.

(57) ABSTRACT

A process for production of a microporous affinity membrane having regioselective affinity for compounds in blood or other biologically active fluids to be removed during purification of blood or said fluids is disclosed, as well as a microporous affinity membrane produced by said process, an adsorption device containing such a microporous affinity membrane, and use of such a microporous affinity membrane.

51 Claims, 3 Drawing Sheets

Membrane adsorption device with regioselectively functionalized microporous hollow fibre membranes

U.S. PATENT DOCUMENTS

| | | | |
|---|---|---|---|
| 5,868,936 A | 2/1999 | Ofsthun et al. | |
| 6,013,789 A | 1/2000 | Rampal | |
| 6,022,902 A * | 2/2000 | Koontz | 521/53 |
| 6,090,292 A | 7/2000 | Zimmermann et al. | |
| 6,245,537 B1 * | 6/2001 | Williams et al. | 435/135 |
| 6,643,749 B2 * | 11/2003 | Marui | 711/154 |
| 7,140,497 B2 * | 11/2006 | Verpoort et al. | 210/507 |
| 7,244,442 B2 * | 7/2007 | Williams et al. | 424/423 |
| 2005/0214162 A1 * | 9/2005 | Muller et al. | 422/57 |

FOREIGN PATENT DOCUMENTS

| | | |
|---|---|---|
| EP | 0341413 B2 | 5/2000 |
| EP | 0695622 | 11/2001 |
| WO | WO80/02805 | 12/1980 |
| WO | WO90/15883 | 12/1990 |
| WO | 97/48483 | 12/1997 |
| WO | WO01/31339 A1 | 5/2001 |

* cited by examiner

PROCESS FOR PRODUCTION OF A REGIOSELECTIVE MEMBRANE

This application is the national stage entry of International Application No. PCT/SE03/00655, filed Apr. 23, 2003, and claims priority to Swedish Application No. 0201207-8, filed Apr. 23, 2002, which is incorporated herein by reference.

TECHNICAL FIELD OF THE INVENTION

The present invention relates to a process for production of a microporous affinity membrane having regioselective affinity for compounds in blood or other biologically active fluids to be removed during purification of blood or said fluids, to a microporous affinity membrane produced by said process, to an adsorption device containing such a microporous affinity membrane, and to use of such a microporous affinity membrane.

BACKGROUND ART

Microporous hollow fibre membranes and flat sheet membranes are examples of microporous affinity membranes having a blood side and a filtrate side. Such membranes are well known for analytical, diagnostic or therapeutical purposes. For example, such microporous hollow fibre membranes and flat sheet membranes are useful for the treatment of blood or other biologically active fluids with a view to eliminating undesired compounds therefrom, i.e. in therapeutic apheresis. Microporous hollow fibre membranes are normally composed of a bundle of separate microporous hollow fibres. For detoxification of whole blood, e.g. dialysis and plasmapheresis, the membrane bundle is normally potted at each end of a polycarbonate tube fitted with two ports in a shell. The blood is normally extracorporeally pumped through a lumen representing the blood side, of each fibre, and a part of the blood plasma penetrates, i.e. is filtrated, through the pores of the fibre wall into an outer compartment representing the filtrate side, surrounding each fibre in the bundle. The concentrated blood containing blood cells, too large to enter the pores, and the remaining non-filtered part of blood plasma passes through the lumen. In a venous blood line the filtrated blood plasma stream is normally added to the non-filtered blood stream and returned to the patient.

With a view to eliminating undesired compounds from the blood, the surfaces and pores of the microporous affinity membranes, e.g. microporous hollow fibre membranes and flat sheet membranes, are provided with activated sites or ligands specific for binding to the undesired blood compounds to be eliminated. Such activated sites or ligands are normally based on or bound to functional groups, e.g. amino, carboxy, or sulfonic acid groups, on the microporous membrane surface. The undesired compounds to be eliminated from the blood are normally toxins of different kinds, e.g. bacterial derived toxins. Further examples of such undesired compounds are presented below.

The lumen surfaces on the blood side of microporous hollow fibre membranes, the surfaces on the blood side of flat sheet membranes, the surfaces of the pores and the surfaces on the filtrate side of such membranes are often provided with such activated sites or ligands, particularly for purification of blood or biologically active fluids.

In blood purification applications activated sites or ligands, e.g. positive amino groups as functional groups for heparin or endotoxin adsorption, on the surface on the blood side of such membranes may activate certain blood constituents, e.g. thrombocytes. In such a case, these blood constituents are activated and/or adhered to the ligands and are significantly reduced from the blood. Such an adhesion is undesired. Other blood constituents, e.g leucocytes, red blood cells and proteins, may in some extent also be adhered to such ligands or activated sites on the blood side of the membrane.

This undesired activation of blood constituents in such membranes has since long been a great problem, in particular the accompanying undesired elimination of thrombocytes from the blood. Several attempts have been made to solve this problem to prepare microporous hollow fibre membranes and flat sheet membranes lacking the above-mentioned ligands or activated sites on the blood side of the membrane, but so far only complicated processes requiring large amounts of reaction chemicals and solvents have been found. Moreover, these processes are also expensive, ineffective and not environmental friendly, thereby creating problems highly needed to solve.

WO 80/02805 describes, inter alia, a process for the treatment of and/or removal of undesired compounds from whole blood and a membrane therefor. A biologically activated material is immobilised, i.e. ligands are arranged in the pores, and/or on the surface of said membrane that faces away from said whole blood, i.e. faces the filtrate side of the membrane. Further, processes for immobilising different kinds of biologically active material, i.e. ligands, by treatment with chemicals are disclosed. Thus, an asymmetric immobilisation, i.e. creation of regioselective affinity, is disclosed with a view to avoiding contact between blood corpuscles and the immobilising reagent and, thus, pyrogen and/or anaphylactic reactions.

U.S. Pat. No. 5,868,936, WO 97/48483, U.S. Pat. No. 5,766,908, and EP-A2-0,341,413 disclose immobilising techniques for attaching ligands to the surface of the pores in hollow fibre membranes.

U.S. Pat. No. 6,090,292 discloses an asymmetric dialysis hollow fibre coated with albumin essentially on the side facing away from the blood, i.e. facing the filtrate side.

Plasma treatment is known as an effective method for modification of surfaces. It is, inter alia, used to increase the wettability and thus the adsorption properties of surfaces.

EP-A1-0,683,197, U.S. Pat. Nos. 6,022,902, 5,591,140, and 6,013,789 disclose treatment of a surface with plasma with a view to immobilising certain ligands.

U.S. Pat. No. 5,597,456 discloses atmospheric pressure plasma treatment of surfaces of medical devices.

EP-A2-0,695,622 discloses plasma modification of flat porous articles using low pressure plasma treatment.

SUMMARY OF THE INVENTION

The object of the present invention is to solve the above problem with defective procedures for production of microporous affinity membranes having regioselective affinity for undesired compounds in blood or other biologically active fluids with a view to avoiding undesired activation of constituents in blood or other biologically active fluids in microporous affinity membranes during the purification treatment of blood or said fluids.

This object is achieved with a microporous affinity membrane, produced by a process for production of a microporous affinity membrane having regioselective affinity for compounds in blood or other biologically active fluids to be removed during purification of blood or said fluids, wherein a microporous affinity membrane substrate having a blood side and a filtrate side is subjected to one or more cycles of plasma ignition in the presence of a gas mixture comprising a functional group containing modifying gas, wherein functional groups are regioselectively bound to pore surfaces of the microporous affinity membrane substrate. In a further process step ligands having affinity for said compounds in blood or said fluids may be bound to the functional groups.

In one embodiment functional groups are also regioselectively bound to surfaces on the filtrate side of the microporous affinity membrane substrate.

The present invention also relates to a microporous affinity membrane produced by said process, to an adsorption device containing such a microporous affinity membrane and to use of such a microporous affinity membrane.

Other objects, features, advantages and preferred embodiments of the present invention will become more apparent from the following detailed description when taken in conjunction with the drawings and the appended claims.

DETAILED DESCRIPTION OF PREFERRED EMBODIMENTS

Figure 1:
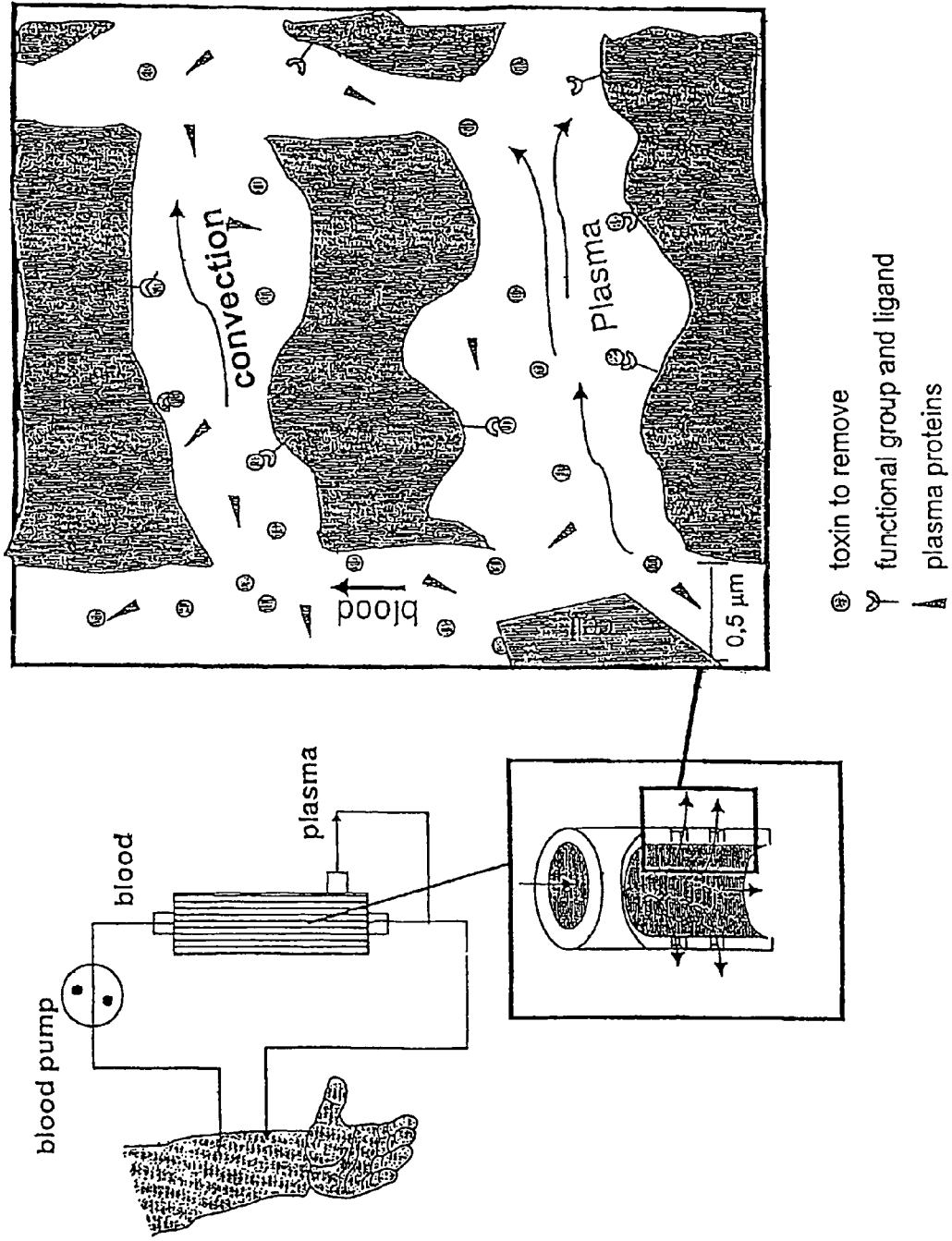
FIG. 1 shows a system comprising a microporous membrane adsorption device with regioselectively functionalized microporous hollow fibre membranes produced according to a preferred embodiment of the present invention and having functional groups with ligands bound thereto. Further, in the right part of FIG. 1 such a membrane is shown in an enlarged cross-sectional view.

In a preferred embodiment the present invention relates to a process for production of a microporous hollow fibre membrane having regioselective affinity.

In another preferred embodiment the present invention relates to a process for the preparation of a microporous flat sheet membrane having regioselective affinity.

Throughout the application text and the claims the following abreviations are used.

PES=polyethersulfone
PVP=polyvinylpyrrolidone
PP=polypropylene
DACH=diaminocyclohexane
DETA=diethylenetriamine
ESCA=electrospectroscopy for chemical analysis
PFBA=pentafluorobenzaldehyde
sccm=standard cubic centimeter The term "functional group containing modifying gas" or "modifying gas" used throughout the application text means the gaseous form of the molecule leading to surface modification during gas plasma treatment. In the gas plasma these molecules comprising the functional groups are converted to activated species, i.e. radicals or ions. During the gas plasma treatment there is a surface retention of functional groups resulting in a functional membrane surface, i.e. a membrane with regioselective affinity, having the ability to covalently bind different ligands.

The term "blood" used throughout the application text is intended to cover whole blood and different modifications thereof in which one or more of the constituents thereof have been separated off.

The term "other biologically active fluids" used throughout the application text means pharmaceutically useful solutions or pharmaceutical preparations which contain a biologically active component, such as a coagulation factor.

The term "blood side" used throughout the application text means the membrane side on which blood or another biologically active fluid is brought to flow during purification by use of a microporous affinity membrane, i.e. either the outer (shell) side or the inner (lumen) side of a microporous hollow fibre membrane, and either of the two sides of a microporous flat sheet membrane.

The term "filtrate side" used throughout the application text means the membrane side on which the filtered part of blood or another biologically active fluid reaches after having passed through the pores of a microporous affinity membrane, i.e. either the outer (shell) side or the inner (lumen) side of a microporous hollow fibre membrane, and any of the both sides of a microporous flat sheet membrane.

The term "compound in blood . . . " used throughout the application text means an undesired compound intended to be removed from the blood.

The terms "blood constituent" and "constituents in blood" used throughout the application means components normally existing in blood, e.g. different blood cells and proteins.

The term "gas mixture" used throughout the application text means the mixture between modifying gas and carrier gas, but is also used, for simplicity reasons, for the embodiment when the carrier gas is absent.

The term "gas plasma mixture" used throughout the application means the medium resulting from the plasma ignition of the gas mixture and containing the activated species providing the binding of functional groups to the surfaces in question.

The terms "microporous affinity membrane substrate" and "membrane substrate" used throughout the application text means an untreated, not functionalised microporous affinity membrane, i.e. lacking regioselective affinity and intended as a start material in the process according to the present invention.

The term "microporous hollow fibre membrane" used throughout the application text is intended to cover everything from one microporous single hollow fibre up to several single hollow fibres and one or more bundles of such microporous hollow fibres, each fibre having a filtrate side and a blood side.

The term "microporous flat sheet membrane" used throughout the application text means a micropore containing flat membrane having a filtrate side and a blood side.

In one preferred embodiment of the present invention microporous hollow fibre membranes are regioselectively modified or functionalised only on the outer surface, i.e. the filtrate side, and on the surfaces within the pores in an improved way compared to known techniques.

The membrane lumen surface, i.e. on the blood side, which comes into contact with whole blood when the membranes are used for blood treatment in therapeutic apheresis, is to remain unmodified. This is achieved by avoiding affinity on the blood side, thereby inhibiting the interaction between certain blood constituents and the ligands bound to functional groups introduced regioselectively during the membrane modification process. This is an important requirement for selective removal of compounds from whole blood or other biologically active fluids within a membrane adsorption device.

Referring to FIG. 1 the right part thereof shows a preferred embodiment of a regioselective microporous hollow fibre membrane for treatment of blood in an enlarged cross-sectional view. The flow of blood is marked with an arrow on the blood side. The membrane wall pores connects the blood side with the filtrate side. The flow of blood plasma containing the compounds to remove from blood is marked with arrows in the pores. On the surfaces of the pores and on the outer surface on the filtrate side functional groups, to which ligands are attached, have been bound. To some of said ligands compounds to be eliminated have been bound. As appears, no functional groups are attached to the lumen surface on the blood side.

A major advantage of the present invention compared to prior art, e.g. WO 80/02805, is that the need for reaction chemicals and solvents is highly reduced and that the total costs, e.g. the cost for disposal of chemicals, is lowered. Moreover, the present invention provides a more environmentally friendly process compared to prior art processes for the production of such regioselective membranes. The present invention does not require any organic solvent or chemicals that need to be eliminated after the treatment, i.e. the gas mixture used reacts totally and no side products are left to be taken care of afterwards.

Further advantages of the present invention include that the microporous affinity membranes having regioselective affinity are much easier to manufacture compared to the conventional wet-chemical approaches. This is due to the gas plasma treatment process. Moreover, the present invention provides high versatility in that a variety of different functional groups can be arranged to immobilise compounds to be eliminated. This is possible due to independence of the chemicals used in prior art processes. By means of the gas plasma treatment it is possible to introduce reactivity in almost all molecules as long as the molecules can ignite to plasma, which is why a wide variety of functional groups may be chosen. Further, high efficiency due to improved mass transport properties is obtained, i.e. convective transport of blood compounds to eliminate, e.g. toxins, that bind to the binding sites, i.e. ligands, compared to the corresponding diffusion transport in affinity columns.

In another preferred embodiment of the present invention a microporous flat sheet membrane having regioselective affinity is produced with a process corresponding to the process for preparing microporous hollow fibre membranes having corresponding properties. This process is described in detail below, e.g. in Example 3.

The functional groups to be introduced on the membrane substrate surfaces of interest are preferably amino groups originating from such molecules as amino compounds (diamines, triamines), e.g. diaminocyclohexane (DACH) and diethylenetriamine (DETA), preferably diaminocyclohexane, but also from all organic precursors with primary amino groups or mixtures of hydrogen with nitrogen or ammonia, provided their vapour pressure is high enough to give a substantial amount of the molecule containing the functional groups in the vapour phase. Further, other functional groups than amino groups can be introduced, e.g. carboxyl, hydroxyl, sulfonic acid, ester or epoxy groups, when precursors comprising corresponding functions are used instead of compounds containing amino functions.

The microporous affinity membranes produced according to the present invention are made of a biocompatible polymeric material, e.g. polyethersulfone (PES), polyvinylpyrrolidone (PVP), polypropylene (PP), polysulfone (PSU), polymethylmethacrylate (PMMA), polycarbonate (PC), polyacrylonitrile (PAN), polyamide (PA), polytetrafluoroethylene (PTFE), cellulose acetate (CA), cellulose nitrate or regenerated cellulose.

The inner diameter of the hollow fibres is normally 200-1000 µm, the wall thickness is normally 20-200 µm and the pore diameter 0.1-2.0 µm. The fibres are normally arranged in modules e.g. containing a bundle of 10 to more than 1000 fibres, but single hollow fibres are also possible to treat. Experimental modules contain 10-100 fibres. Final modules for blood treatment contain more than 1000 fibres. Modules with more fibres may also be modified according to this procedure.

According to the present invention the hollow fibres used for the microporous hollow fibre membrane are preferably made of a blend of polyethersulfone and polyvinylpyrrolidone with an inner diameter of 330 µm, a wall thickness of 110 µm and a pore diameter of 0.4 µm.

The flat sheet membrane is preferably made of a mixture of polyethersulfone and polyvinylpyrrolidone with a wall thickness of 20-200 µm, preferably 110 µm, and a pore diameter of 0.1-0.8 µm, preferably 0.4 µm.

As stated above, the regioselective introduction of amino groups, i.e. the preferred functional groups, only on the pore surfaces, in practice gradually less towards the blood side, and on the filtrate side, but not at all on the blood side of the microporous affinity membrane substrate, is achieved by gas plasma treatment of the membrane substrate, preferably using DACH or DETA, most preferably DACH, as the functional group containing modifying gas, and a stabilising carrier gas, which is chemically inert during the gas plasma reaction. Preferably helium is used as carrier gas due to the wide pressure range used for ignition of gas plasma. The use of low gas plasma power is beneficial with respect to the preservation of the functional groups. As alternative carrier gases nitrogen, hydrogen and argon or corresponding mixtures may be used. A further possibility is to work without any carrier gas. During the gas plasma treatment this mixture of modifying gas and carrier gas includes the activated species described above and provides the regioselective introduction of the amino groups on the surfaces of interest, however, not on the blood side of the microporous affinity membrane substrate, due to deactivation of activated species on the way from the plasma glow discharge zone to the blood side. The proportion between the functional group containing modifying gas and the carrier gas is normally 1:10-1:1, preferably 1:4.

The most important parameters are the direction of the gas plasma mixture flow in relation to the membrane substrate to be treated, the mean free path length of the activated species and the flow rate of the gas plasma mixture.

The ligands to be bound to the functional groups introduced on the surface of the membrane substrate filtrate side and on pore surfaces are chosen dependent on the type of compounds to be removed from the blood or any other biologically active fluid. Examples of ligands are proteins, peptides, amino acids, carboxylic acids, oligonucleotides and mixtures of two or more thereof or any other convenient biomolecules. The ligands are added to the functional groups in a separate wet-chemical process, known per se.

Some basic principles behind the plasma ignition (plasma glow discharge) processes used in connection with the present invention will now be discussed.

Plasma can be ignited when the dimension of the gas containment is much higher than the mean free path length at a given gas pressure. The mean free path length is inversely proportional to the gas pressure. In the low pressure case the mean free path length is dependent on the gas type or composition, ranging from 60 µm to about 400 µm.

With the pore diameter and the membrane wall thickness of the membrane structure to be treated according to the present invention, plasma ignition will normally take place only on the outer side of the membrane or, in certain circumstances, e.g. in the presence of helium, on the lumen side, when the contact between the excited gas molecules and the wall is minimised due to an axial laminar helium gas flow and application of a wobbling frequency with high harmonic overtone additives. When there is no pressure gradient between the outer side of the membrane and the lumen side, the activated particles can enter the pore structure only by diffusion from the plasma zone (may be outside in most cases, or from the lumen side in special cases). The diffusing activated particles will collide with gas molecules and with the walls of the pores on their way from the plasma zone into the pore structure and dissipate their energy. The amount of gas molecule or wall contacts which is necessary for losing the activating energy could previously only be determined empirically. In consequence, there will be a decreasing chemical modification density of the pore walls from the plasma zone area into the membrane structure. The chemical plasma modification density distribution can be influenced by the pore geometry, the plasma intensity, the pressure, the gas composition, the pressure difference over the membrane structure, and the power spectrum of electric frequency input.

The regioselective introduction of the functional groups can be achieved in four different ways for microporous hollow fibre membrane substrates, comprising four different embodiments of the process according to the present invention, as appears from FIGS. 2a-2d, i.e. 2a) outside low pressure treatment (diffusion control) 2b) outside high pressure treatment (laminar or convective control) 2c) inside low pressure treatment (laminar or convective control) 2d) inside high pressure treatment (diffusion control)

Figure 2:
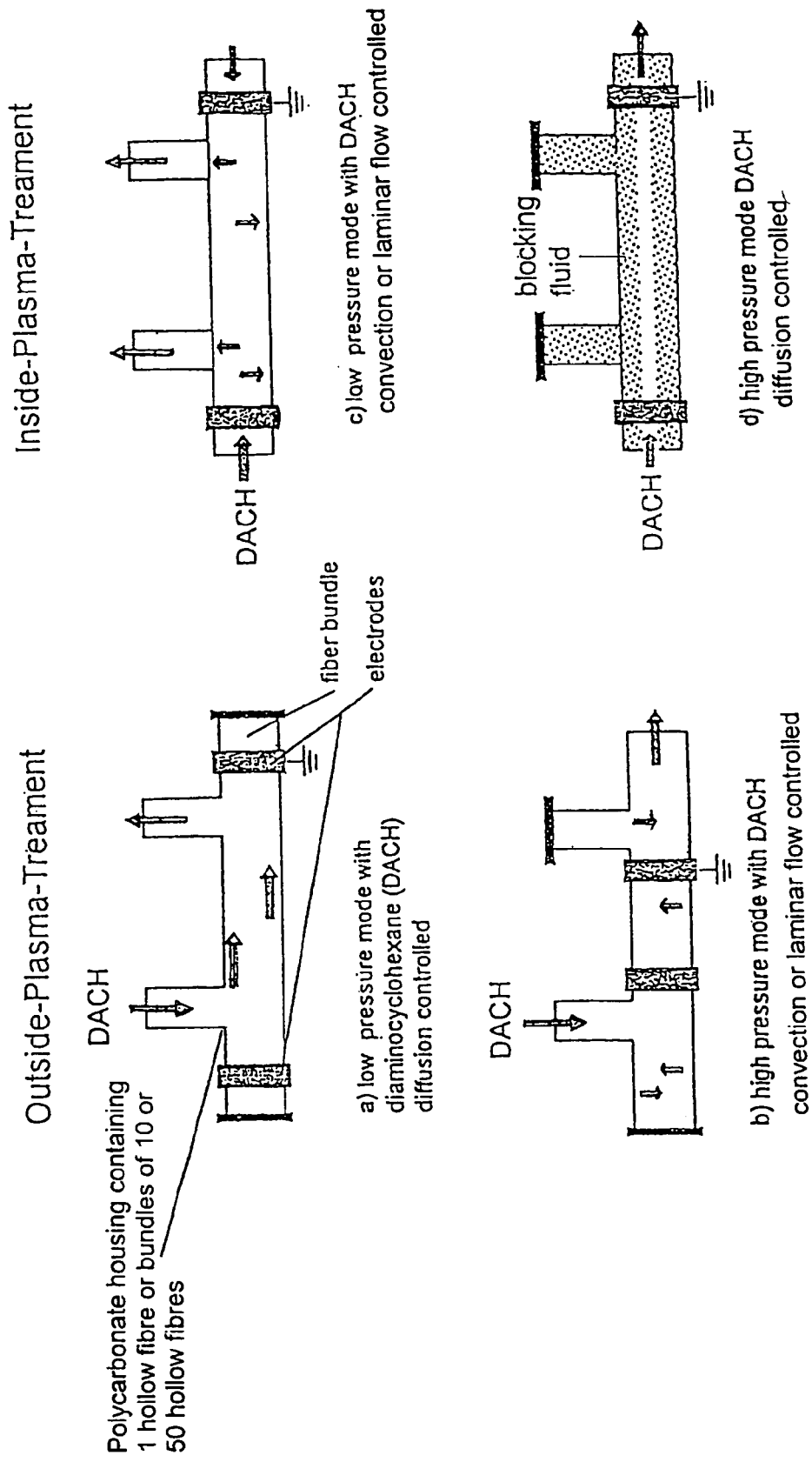
FIG. 2a shows outside plasma treatment of a membrane substrate at low pressure.
FIG. 2b shows outside plasma treatment of a membrane substrate at high pressure.
FIG. 2c shows inside plasma treatment of a membrane substrate at low pressure.
FIG. 2d shows inside plasma treatment of a membrane substrate at high pressure.

The processes shown in FIGS. 2a and 2b represent a first main mode and provide a regioselective functionalisation of the outer surface and the pore surface; the processes shown in FIGS. 2c and 2d represent a second main mode and provide a regioselective functionalisation of the inner surface and the pore surface. Thus, these four different embodiments (or two main modes) are intended for different uses, i.e. depending on if the lumen surface is intended to be on the blood side or the filtrate side of the microporous hollow fibre membrane.

As appears from FIG. 2a, showing one embodiment of outside low pressure treatment, diffusion controlled outside plasma treatment under low pressure (0.1-10 mbar), preferably about 1.6 mbar (0.3 mbar modifying gas)) is performed by adding the gas mixture to the outside of the microporous hollow fibre membrane substrate. A fibre module of a hollow fibre membrane substrate is placed between two electrodes, preferably ring electrodes, around a polycarbonate housing. Openings in the housing allow a gas flow along the outer surface of the membrane substrate. After appropriate evacuation the gas mixture is introduced and ignition is performed creating a gas plasma mixture. The gas plasma mixture penetrates the membrane substrate structure by diffusion, i.e. the driving force from mass transfer equals the concentration gradient. The process preferably involves one to ten cycles of plasma ignition at 13.56 MHz during 1 to 10 sec under the gas mixture atmosphere, followed by a plasma-off period of 2-3 minutes. During the flow of the gas plasma mixture functional groups, e.g. amino groups, are attached to the outer surfaces and the pore surfaces of the hollow fibre membrane substrate. Finally, the fibre modules are evacuated for 1-60 min, normally about 15 min, to remove non-adsorbed modifying gas present in the gas mixture. The inlet and outlet openings for the gas mixture are preferably located at the opposite ends of the housing. This embodiment gives highly satisfactory results as to regioselective affinity for a hollow fibre membrane for whole blood treatment and is therefore the most preferred embodiment of the present invention.

As appears from FIG. 2b outside plasma treatment under high pressure (50 mbar-1.1 bar) is performed in the same way as for the low pressure treatment except for the fact that the gas plasma mixture penetrates the membrane substrate structure by convection or laminar flow.

As appears from FIG. 2c convection or laminar flow controlled inside plasma treatment under low pressure (0.01-50 mbar) is performed by adding the gas mixture into both ends of the fibre bundle, wherein the gas mixture penetrates the pores from the lumen side to the outer side of the hollow fibres, i.e. to the polycarbonate housing space, and then exits the housing space through the gas mixture exits arranged perpendicular or substantially perpendicular to the fibre bundle direction. Further, the electrodes are preferably arranged in such a way that the gas mixture exits are arranged between the electrodes.

As appears from FIG. 2d diffusion controlled inside plasma treatment under high pressure (50 mbar-1.1 bar) is performed by adding gas mixture at one end of the fibre bundle, wherein the gas mixture exits shown in FIG. 2c are closed and the concentric polycarbonate housing or casing surrounding the fibre bundle is filled with a blocking fluid, e.g polyethylene glycole, thereby allowing the gas mixture to more or less fill the pores but preventing it from passing out from the pores to the outer surface. Instead, the gas mixture exits the fibre bundle at the opposite end.

In the process for preparation of a microporous hollow fibre membrane according to the present invention, the ignition frequency during the plasma ignition is 1 kHz-13.56 MHz or multiples of 13.56 mHz or microwave frequency, the power is 0.5-20 W, the voltage of the electrodes is 50-500 volts, the pressure is 0.01-10 mbar, the flow rate is 0.1-200 sccm/min, and the gas plasma mixture flow period is up to 20 min.

The plasma treatment experiments and the analyses described below were carried out, if not otherwise stated, for a microporous hollow fibre membrane having regioselective affinity produced according to the most preferred embodiment according to the present invention, i.e. wherein DACH/ helium as gas mixture was added to the membrane substrate during the plasma treatment.

For microporous flat sheet membranes the regioselective introduction of the functional groups is achieved as follows.

Figure 3:
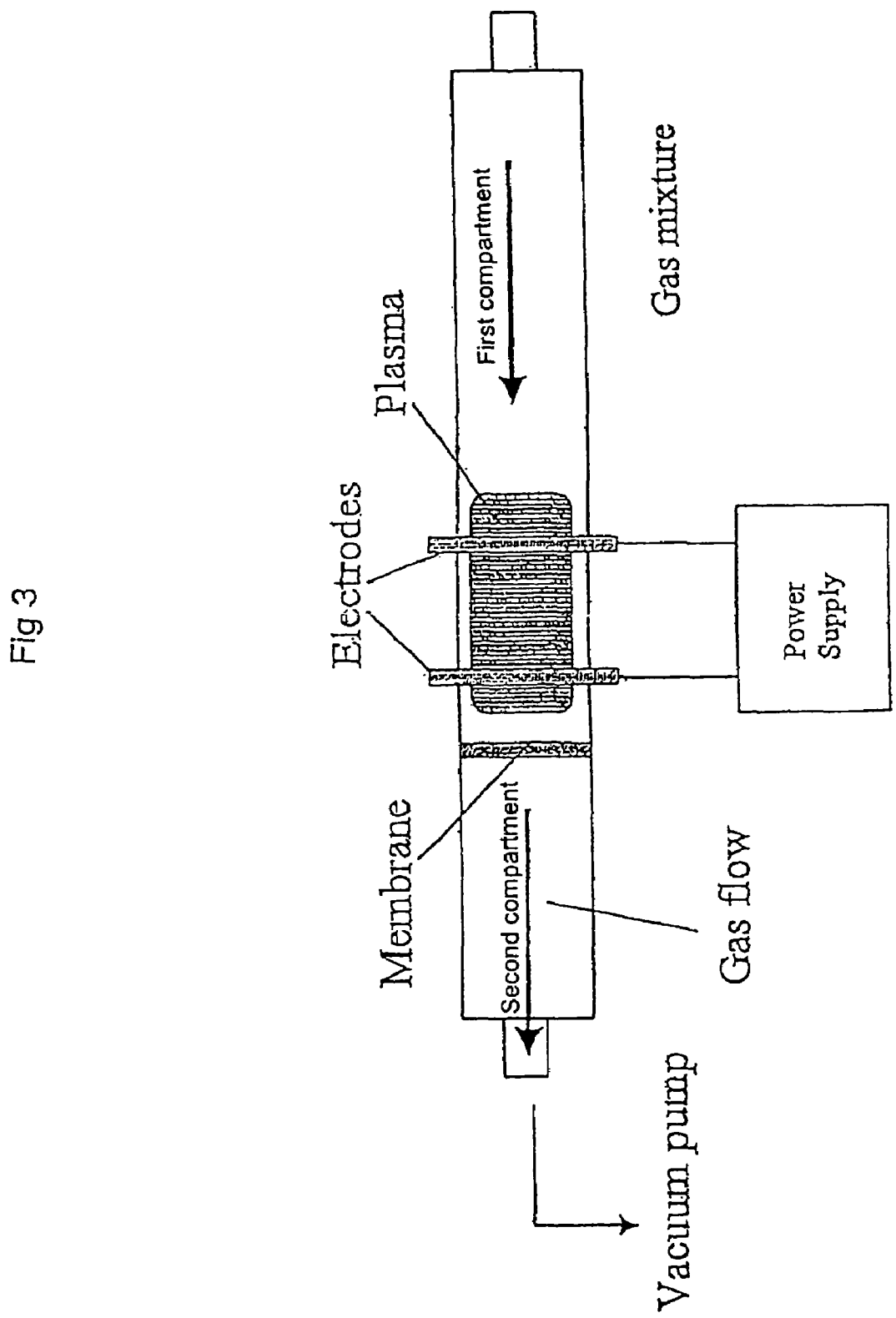
FIG. 3 shows plasma treatment of a microporous flat sheet membrane substrate according to another embodiment of the present invention.

FIG. 3 shows the preparation of a microporous flat sheet membrane having regioselective affinity for undesired compounds in blood or other biologically active fluids by use of plasma ignition. The flat sheet membrane substrate is enclosed in a housing or casing, having a first and a second compartment separated from each other by the flat sheet membrane substrate. During the plasma ignition treatment the gas mixture is initially introduced in the first compartment, also comprising a plasma chamber with two electrodes connected to a power supply. After the plasma ignition of the gas mixture the gas plasma-mixture obtained flows against and passes the flat sheet membrane substrate perpendicularly arranged in relation to the gas plasma mixture flow. The flat sheet membrane substrate surface facing the first compartment, i.e. on the intended filtrate side of said membrane substrate, and the pore surfaces are regioselectively provided with functional groups. No functional groups are bound to the flat sheet membrane substrate surface facing the second compartment, i.e. on the intended blood side of the membrane. Excess gas continues to flow through the second compartment and is then evacuated therefrom. A vacuum pump connected to the second compartment provides the flow through the whole arrangement. Appropriate ligands are then bound to the functional groups in a conventional way.

In the process for preparation of a microporous flat membrane according to the present invention, the ignition frequency during the plasma ignition is 1 kHz-13.56 MHz or multiples of 13.56 mHz or microwave, the power is 1-20 W, preferably about 5 W, the voltage of the electrodes is 50-300 volts, the pressure is 0.1-5 mbar, preferably about 0.3 mbar, the flow rate is 1-100 sccm/min, preferably 10 sccm/min, and the gas plasma mixture flow period is up to 30 min, preferably about 5 min. The parameters during this plasma ignition treatment are further described in Example 3.

It is to be understood that the housings or casings, inlets, outlets, electrodes etc in the devices shown in FIGS. 2a-2d and 3 may be altered as to size, mutual arrangement, type and geometry, still giving the beneficial effects desired for the present invention.

An electron spectroscopy for chemical analysis (ESCA) was performed with a view to quantitatively evaluating the amino group distribution resulting from the plasma treatment.

First a sample of a microporous affinity membrane with regioselective affinity is illuminated with Al k-alpha rays (1486.6 eV), and the energy of emitted electrons is measured. Fluorine is used only as a marker for the functionality arranged at the membrane surfaces, which itself does not contain any fluorine. Instead, the membrane surface functionalities are derivatised with a fluorine containing compound, e.g. pentafluorobenzaldehyde, with a view to quantifying the functional groups bound to the membrane surfaces.

The derivatisation procedure is preferred as follows: 300 μl stock solution of 0.1 M PFBA in pentane is added to 15 ml pentane. After addition of the test material the solution is brought to react during 2 hours at 39° C. in a water bath and under reflux. This is followed by washing during the night in pentane in a Soxhlet device at 43° C. (one cycle: 20 min).

In the table below the distribution of atoms in the functional groups on the outer (shell) and inner (lumen) surface of microporous hollow fibre membranes is shown. It appears that, due to the preferred embodiment of the process according to the present invention, the presence of primary amino groups on the inner surface is zero (no fluorine-signal!). The 1.4 atom % nitrogen is due to the PVP content of the membrane.

TABLE

Atom distribution (ESCA) of plasma-modified PES/PVP
membranes after derivatisation with pentafluorobenzaldehyde

| Surface | Distribution of elements [%] | | | | |
|---|---|---|---|---|---|
| | C | O | S | N | F |
| Shell | 73.0 | 10.2 | 0.7 | 8.3 | 7.8 |
| Lumen | 74.5 | 21.7 | 2.4 | 1.4 | — |

Further, an ESCA analysis was performed with a PP membrane treated with different plasma treatment modes. The table below shows the atom distribution of plasma treated (DACH) PP membrane substrates on inner (lumen) and outer (shell) surfaces of hollow fibre membranes.

Atom Distribution (ESCA) of Plasma Treated (DACH) PP Membranes

N may here be used as marker as PP does not contain N.

| Treatment mode | Surface | Distribution of elements [%] | | |
|---|---|---|---|---|
| | | C | O | N |
| Gas stream outside, parallel to fibres (diffusion controlled) | shell | 90.0 | 6.9 | 3.1 |
| | lumen | 94.8 | 5.2 | — |
| Gas stream through the membrane wall of hollow fibre (convection controlled) | shell | 84.7 | 7.2 | 8.1 |
| | lumen | 94.2 | 4.5 | 1.3 |

This indicates an approximate 5-fold surplus of amino groups on the outer surface relative to the inner surface for a convection controlled process and the absence of amino groups on the inner surface for a diffusion controlled process.

Moreover, the table below shows the concentration of introduced active amino groups depending on the treatment mode used to introduce them for a PES/PVP hollow fibre membrane.

| Treatment mode | $NH_2$ concentration [mmol/g] |
|---|---|
| Outside plasma, low pressure (FIG. 2a) | 0.08-0.09 |
| Outside plasma, high pressure (FIG. 2b) | 0.03 |
| Inside plasma, low pressure (FIG. 2c) | 0.02 |
| Inside plasma, high pressure + blocking fluid (FIG. 2d) | 0.06 |

The highest concentrations are achieved with the outside plasma/low pressure mode treatment (see FIG. 2A). These concentrations come close the ones required for the monomolecular immobilisation of peptides of several 1000 Da.

Thus, regioselective modification of membrane substrates with a higher selectivity for the outer surface can be achieved. This makes the membranes interesting for arranging ligands selectively on their surfaces. As stated above the regioselectively arranged ligands enable a selective removal of toxins or other target compounds by adsorption during therapeutic purification of blood or other biologically active fluids, while the interaction of constituents in blood or such fluids with the ligands or adsorbed toxins is avoided.

Examples of compounds of interest to remove from blood or other biologically active fluids are e.g. endotoxins and inflammatory mediators in septic patients, pathogenic antibodies in several immune diseases, low-density lipoproteins in patients with coronary heart disease and drug resistant hypercholesterolemia, and fibrinogen used for the treatment of microcirculatory disorders.

The present invention also relates to use of the microporous affinity membrane produced according to the present invention and having regioselective affinity in therapeutic apheresis, for diagnostic applications when enrichment of trace materials is necessary (e.g. pesticides in food or water, metabolites and drugs in plasma, urine, and saliva), and for drug development applications. Common for these different applications is that blood constituents are not activated during the use of the microporous affinity membrane.

In the following examples of the process according to the present invention, functionalisation, i.e. providing regioselective affinity, with amino groups for a single hollow fibre, a fibre bundle modification and a flat sheet membrane substrate, respectively, is shown for PES-PVP microfiltration membranes.

EXAMPLE 1

Single Hollow Fibre Modification

The plasma treatment mode shown in FIG. 2a) was used. The fibre length was 15 cm and the tube diameter 1.2 cm. The system was evacuated at a pressure below 0.01 mbar during 15 min. DACH was added at a flow rate of 0.5 sccm/min; applicable range: 0.1-200 sccm/min) at a pressure of 0.3 mbar (applicable range: 0.1-10 mbar). The plasma ignition was performed at 13.56 MHz (1 kHz to 13.56 MHz) and multiples of 13.56 MHz and microwave at 15 W (applicable range: 0.5-200 W) during 1 sec (applicable range: 0.1 sec-10 min). After the plasma treatment step the system was flushed with $H_2$ at 10 mbar during 5 min, followed by venting with $N_2$ to minimize oxidation of the membrane.

EXAMPLE 2

Fibre Bundle Modification (50 Hollow Fibres)

The steps in Example 1 were repeated with the exceptions that 2 sccm/min (applicable range: 1-100 sccm/min) helium was added as carrier gas together with the DACH, that the total pressure was 1.2 mbar (applicable range: 0.1-10 mbar), that the effect at the plasma ignition step was 2 W (applicable range: 1-20 W) and that the plasma time was 15 min (applicable range: 10 sec-30 min). This parameter set results in proper amino functionalisation of outer surfaces and inner pore surfaces of all 50 hollow fibres.

EXAMPLE 3

Modification of a Microporous Flat Sheet Membrane Substrate

The plasma treatment mode according to FIG. 3 was used. The system was evacuated at a pressure below 0.01 mbar. $H_2$ was added at a flow rate of 10 sccm/min together with DACH at a total pressure of 0.3 mbar. The plasma ignition was performed at 13.56 MHz and an effect of 5 W and the plasma time was 5 min.

The result obtained is a flat sheet membrane regioselectively functionalised with amino groups on the surface on the filtrate side and on the pore surfaces, but not on the surface on the blood side.

The invention claimed is:

1. A process for production of a microporous affinity membrane having regioselective affinity for compounds in blood or other biologically active fluids to be removed during purification of blood or said biologically active fluids, comprising subjecting a microporous affinity membrane substrate having a blood side and a filtrate side to one or more cycles of plasma ignition in the presence of a gas mixture comprising at least one modifying gas, wherein the modifying gas comprises an organic precursor with at least one functional group, wherein the at least one functional group comprises an amino, aldehyde, ester, epoxy, hydroxyl, and/or sulfonic acid group, wherein the at least one functional group is regioselectively bound to pore surfaces of the microporous affinity membrane substrate.

2. The process according to claim 1, wherein the microporous affinity membrane substrate is a microporous hollow fibre membrane substrate.

3. The process according to claim 2, wherein the microporous hollow fibre membrane substrate is enclosed in a housing or a casing throughout the process.

4. The process according to claim 3, wherein the gas mixture is added to the housing or casing space surrounding the outer surface of the microporous hollow fibre membrane substrate in a diffusion controlled way at a pressure of 0.01-50 mbar.

5. The process according to claim 3, wherein the gas mixture is added to the housing or casing space surrounding the outer surface of the microporous hollow fibre membrane substrate in a laminar flow or convection controlled way at a pressure of 50 mbar-1.1 bar.

6. The process according to claim 3, wherein the gas mixture is added to the lumen of the microporous hollow fibre membrane substrate in a diffusion controlled way at a pressure of 50 mbar-1.1 bar, and wherein the housing space surrounding the outer surface of the microporous hollow fibre membrane substrate is filled with a blocking fluid.

7. The process according to claim 3, wherein the housing or casing is concentric in relation to the membrane substrate.

8. The process according to claim 2, wherein the plasma ignition results in a gas plasma mixture flowing axially along the outer or inner surface of the microporous hollow fibre membrane substrate.

9. The process according to claim 2, wherein the microporous hollow fibre membrane substrate is made up of a mixture of polyethylenesulfide and polyvinylpyrrolidone having an inner diameter of 200-1000 µm, a wall thickness of 20-200 µm, a pore diameter of 0.1-0.8 µm, or modules of more than 1000 fibres.

10. The process according to claim 2, wherein the ignition frequency during the plasma ignition is 1 kHz-13.56 MHz or multiples of 13.56 mHz or microwave frequency, the power is 0.5-20 W, the voltage of the electrodes is 50-500 volts, the pressure is 0.01-10 mbar, the flow rate is 0.1-200 sccm/min, and the gas plasma mixture flow period is up to 20 mm.

11. The process according to claim 2, wherein the gas mixture is added to the lumen of the microporous hollow fibre membrane substrate in a laminar or convection controlled way at a pressure of 0.01-50 mbar.

12. The process according to claim 2, wherein the microporous hollow fibre membrane substrate is made up of a mixture of polyethylenesulfide and polyvinylpyrrolidone having an inner diameter of about 330 µm, a wall thickness of about 110 µm, a pore diameter of about 0.4 µm, and is assembled in modules each having 1 hollow fibre or assembled in bundles or modules of more than 1000 fibres.

13. The process according to claim 2, wherein the microporous hollow fibre membrane substrate is assembled in bundles or modules of up to 1000 fibres.

14. The process according to claim 1, wherein the microporous affinity membrane substrate is a microporous flat sheet membrane substrate.

15. The process according to claim 14, wherein the microporous flat sheet membrane substrate throughout the process is enclosed in a housing or casing having a first and a second compartment separated from each other by said membrane substrate, wherein the surface on the filtrate side of said membrane substrate is facing the first compartment and the surface of the blood side is facing the second compartment, and wherein the gas mixture is added to said first compartment and the functional groups during the plasma ignition in the presence of the gas mixture are bound to pore surfaces and the surface on the filtrate side of the microporous flat sheet membrane substrate.

16. The process according to claim 15, wherein the plasma ignition results in a gas plasma mixture with a flow rate of 1-100 sccm/min.

17. The process according to claim 16, wherein the flow rate is about 10 sccm/min.

18. The process according to claim 15, wherein excessive gas is evacuated from the housing or casing spaces after the plasma ignition.

19. The process according to claim 14, wherein the microporous flat sheet membrane substrate is made up of a mixture of polyethersulfone and polyvinylpyrrolidone having a wall thickness of 20-200 µm.

20. The process according to claim 19, wherein the microporous flat sheet membrane substrate has a wall thickness of about 110 µm, and a pore diameter of about 0.4 µm.

21. The process according to claim 14, wherein the ignition frequency during the plasma ignition is 1 kHz-13.56 MHz or multiples of 13.56 mHz or microwave, the power is 1-20 W, the voltage of the electrodes is 50-300 volts, the pressure is 0.1-5 mbar, the flow rate is 1-100 sccm/min, and the gas plasma mixture flow period is up to 30 mm.

22. The process according to claim 21, wherein the power is about 5 W, the pressure is about 0.3 mbar, the flow rate is 10 sccm/min, and the gas plasma mixture flow period is about 5 mm.

23. The process according to claim 1, wherein ligands having affinity for compounds in blood or other biologically active fluids are bound to the at least one functional group.

24. The process according to claim 23, wherein the ligands are selected from the group consisting of proteins, peptides, amino acids, carboxylic acids, nucleotides, oligonucleotides, antigens, antibodies, and mixtures of two or more thereof.

25. The process according to claim 1, wherein the at least one functional group is regioselectively bound to surfaces on the filtrate side of the microporous affinity membrane substrate.

26. The process according to claim 1, wherein the at least one modifying gas is diaminocyclohexane (DACH) or diethylenetriamine (DETA).

27. The process according to claim 1, wherein the gas mixture also comprises at least one carrier gas.

28. The process according to claim 27, wherein the at least one carrier gas is chemically inert during the process.

29. The process according to claim 27, wherein the proportion between the at least one modifying gas and the at least one carrier gas is 1:100 to 1:1.

30. The process according to claim 27, wherein the at least one carrier gas comprises helium, nitrogen, hydrogen, argon, or a mixture of two or more thereof.

31. The process according to claim 27, wherein the proportion between the at least one modifying gas and the at least one carrier gas is 1:4.

32. The process according to claim 1, wherein up to 10 cycles of plasma ignitions are performed.

33. A microporous affinity membrane produced according to claim 1, wherein said microporous affinity membrane is a microporous flat sheet membrane substrate made up of a mixture of polyether sulfone and polyvinylpyrrolidone having a wall thickness of 20-200 µm and comprises one or more functional groups, bound only to pore surfaces and the filtrate side of the microporous affinity membrane.

34. The microporous affinity membrane according to claim 33, wherein the at least one functional group comprises an amino group.

35. The microporous affinity membrane according to claim 33, wherein ligands having specificity for the components in blood or other biologically active fluids to be removed are bound to the functional groups.

36. A microporous affinity membrane according to claim 35, wherein the ligands are proteins, peptides, amino acids, carboxylic acids, nucleotides, oligonucleotides, antigens, antibodies, or mixtures of two or more thereof.

37. An adsorption device comprising the microporous affinity membrane according to claim 33.

38. A method of therapeutic apheresis, comprising treating blood or other biologically active fluids with the microporous affinity membrane according to claim 33.

39. The method of claim 38, wherein blood constituents are not activated.

40. A method of diagnosing the presence of a compound in a material comprising blood or other biologically active fluids, food, or water, comprising detecting the compound in the material with the microporous affinity membrane according to claim 33.

41. The method of claim 40, wherein, when detecting the compound in blood or other biologically active fluids, blood constituents are not activated.

42. A method of drug development, comprising detecting a potential drug compound in blood or other biologically active fluids with the microporous affinity membrane according to claim 33.

43. The method of claim 42, wherein blood constituents are not activated.

44. A method of purifying blood or other biologically active fluids, comprising treating the blood or other biologically active fluids with the microporous affinity membrane according to claim 33.

45. The method of claim 44, wherein blood constituents are not activated.

46. The process according to claim 1, wherein the at least one functional group comprises an amino group.

47. A microporous affinity membrane produced according to claim 1, wherein said microporous affinity is a microporous hollow fiber membrane substrate made up of a mixture of polyethylenesulfide and polyvinylpyrrolidone having an inner diameter of about 330 µm, a wall thickness of about 110 µm, a pore diameter of about 0.4 µm, and is assembled in modules each having 1 hollow fibre or assembled in bundles or molecules of more than 1000 fibres.

48. The microporous affinity membrane according to claim 47, wherein the at least one functional group comprises an amino group.

49. The microporous affinity membrane according to claim 47, wherein the at least one functional group is bound to the filtrate side.

50. The microporous affinity membrane according to claim 47, wherein ligands having specificity for the components in blood or other biologically active fluids to be removed are bound to the functional groups.

51. A microporous affinity membrane according to claim 47, wherein the ligands are proteins, peptides, amino acids, carboxylic acids, nucleotides, oligonucleotides, antigens, antibodies, or mixtures of two or more thereof.

* * * * *